United States Patent
Due et al.

(10) Patent No.: US 7,322,926 B2
(45) Date of Patent: Jan. 29, 2008

(54) CENTRIFUGATION DEVICE WITH SWINGABLE SAMPLE HOLDER

(75) Inventors: Jorgen Due, Oelstykke (DK); Karen-Margrethe Krzywkowski, Copenhagen East (DK); Nicholas Oswald, Edinburgh (GB); John Larsen, Hilleroed (DK); Henrik Vennerberg, Birkeroed (DK)

(73) Assignee: Sophion Bioscience A/S, Ballerup (DK)

( * ) Notice: Subject to any disclaimer, the term of this patent is extended or adjusted under 35 U.S.C. 154(b) by 0 days.

(21) Appl. No.: 10/542,564

(22) PCT Filed: Feb. 23, 2004

(86) PCT No.: PCT/GB2004/000718

§ 371 (c)(1),
(2), (4) Date: Jul. 24, 2006

(87) PCT Pub. No.: WO2004/073868

PCT Pub. Date: Sep. 2, 2004

(65) Prior Publication Data

US 2006/0287182 A1   Dec. 21, 2006

(30) Foreign Application Priority Data

Feb. 21, 2003   (GB) .................. 0303913.8

(51) Int. Cl.
*B04B 5/02*   (2006.01)
(52) U.S. Cl. ........................................ 494/20
(58) Field of Classification Search ............. 494/20, 494/21, 31, 33, 85; 422/72
See application file for complete search history.

(56) References Cited

U.S. PATENT DOCUMENTS

| | | | | |
|---|---|---|---|---|
| 2,018,837 A | * | 10/1935 | Collatz ..................... | 494/20 |
| 3,202,348 A | * | 8/1965 | Strohmaier ............... | 494/10 |
| 3,270,563 A | * | 9/1966 | Sharples .................. | 73/865.5 |
| 3,951,334 A | | 4/1976 | Fleming et al. | |
| 4,009,824 A | | 3/1977 | Wright | |
| 4,360,149 A | * | 11/1982 | Hein, Jr. .................. | 494/20 |
| 4,708,940 A | | 11/1987 | Yoshida et al. | |
| 6,491,615 B1 | | 12/2002 | Campbell, Jr. et al. | |
| 6,758,803 B2 | * | 7/2004 | Jang ........................ | 494/10 |
| 2001/0000353 A1 | | 4/2001 | Hoshiba et al. | |
| 2002/0132354 A1 | | 9/2002 | Downs et al. | |
| 2003/0036470 A1 | | 2/2003 | Campbell et al. | |
| 2006/0287182 A1 | * | 12/2006 | Due et al. ................ | 494/20 |

FOREIGN PATENT DOCUMENTS

| | | |
|---|---|---|
| DE | 28 22 446 A | 1/1980 |
| DE | 3425922 A1 * | 1/1986 |

(Continued)

*Primary Examiner*—Charles E. Cooley
(74) *Attorney, Agent, or Firm*—Birch, Stewart, Kolasch & Birch, LLP (57) ABSTRACT

A centrifugal device comprising:
a rotor having a rotor shaft having a longitudinal rotor axis;
a holder having an access end, and a holder axis;
a location mechanism for locating the holder within the centrifugal device, such that the holder is rotatable about the rotor axis, with the holder axis forming a non-zero angle with the rotor shaft axis, the location mechanism accurately locating the access end of the holder within the centrifugal device, wherein the location mechanism comprises a holding pin having an axis that is substantially perpendicular to the rotor axis, the holding pin being rotatable about the rotor axis.

22 Claims, 8 Drawing Sheets

FOREIGN PATENT DOCUMENTS

| | | | |
|---|---|---|---|
| DE | 271 653 A | | 9/1989 |
| DE | 100 17 904 A | | 10/2001 |
| GB | 2098515 A | * | 11/1982 |
| GB | 2130367 | * | 5/1984 |
| GB | 2130367 A | | 5/1984 |
| WO | WO-0021678 A1 | | 4/2000 |

* cited by examiner

CENTRIFUGATION DEVICE WITH SWINGABLE SAMPLE HOLDER

This invention relates to a centrifugation device and particularly, but not exclusively to a centrifugation device which is compatible with a system incorporating a pipetting robot.

BACKGROUND OF THE INVENTION

Centrifugation is used to separate the components of liquid suspensions and mixtures according to their density, using centrifugal force. A centrifuge consists of a rotor, with a sample holder adapted to hold a plurality of sample containers. The sample holder is in the form of a plurality of tubes or buckets which are adapted to receive the sample containers which are in the form of vials or buckets. The tubes or buckets, referred to hereinafter as individual holders, are located around the circumference of the sample holder. The rotor is attached to a motor. In use, the sample containers are loaded into the sample holder, and the rotor is rotated at high speed to exert a centrifugal force that moves the heavier components of the sample to the outside of the rotor. Depending on the application, the sample holder can be at a fixed angle or can be of a "swing-out" type in which the sample holder will swing out to an angled or horizontal position relative to the axis of the rotor shaft when rotation begins. Centrifugation is used in both experimental and industrial processes in a wide range of fields. One very common use is in the field of biology in which it is often necessary to separate biological cells from their liquid media. This step is an integral part of almost every experimental and manufacturing procedure involving cells.

It is becoming more common to alternate procedures relating to the separation of biological cells from their liquid media, and therefore it is often advantageous to be able to use a centrifugal device on a robotic platform for use in a system incorporating a pipetting robot. A pipetting robot is used to automatically extract a fluid from a vessel and to transfer that fluid into a container held in an individual holder forming part of a centrifugal device in order that the components of the fluid can be separated using centrifugal force.

A problem with existing centrifugal devices is that after rotation, the one or more individual holders are randomly positioned relative to their pre-rotation positions. This makes it impossible for such centrifugal devices to be used in conjunction with a pipetting robot, since the robot cannot identify the location of individual samples after rotation.

SUMMARY OF THE INVENTION

According to a first aspect of the present invention there is provided a centrifugal device comprising:
- a rotor having a rotor shaft having a longitudinal rotor axis;
- a holder having an access end, and a holder axis;
- location means for locating the holder within the centrifugal device, such that the holder is rotatable about the rotor axis, with the holder axis forming a non-zero angle with the rotor shaft axis, the location means accurately locating the access end of the holder within the centrifugal device, wherein the location means comprises a holding pin having an axis that is substantially perpendicular to the rotor axis, the holding pin being rotatable about the rotor axis.

Preferably, the holder has a holder radius and the axis of the holding pin is spaced apart from the rotor axis by a distance that is less than the holder radius.

Conveniently, the centrifugal device comprises two holding pins which holding pins are coaxial with one another.

By means of the present invention therefore the end of the holder allowing access to a container held therein is accurately located both before and after rotation. The invention therefore provides a centrifuge device, preferably a single sample device which may be easily integrated into a robot platform. The rotor may be driven by standard commercially available motors and is ideally designed for operations where fluid handling is controlled by an overhead robotic pipette.

Preferably, the or each holding pin extends from the rotor. In such embodiments, the holder comprises one or more recesses engageable with the one or more holding pins.

Alternatively, the or each holding pin extends from the holder and is positioned towards the access end of the holder.

By means of the present invention therefore the access end of the holder is held in a position centred close to but offset from a point which intersects the rotor axis. The invention allows for the access end of the holder to be maintained in this position throughout the centrifugal process, or where more convenient, ensures that the access end of the container is positioned at this location both before and after the centrifugal process, even if the access end moves away from this position during rotation.

Advantageously, the centrifugal device further comprises grounding means for electrically grounding the holder.

Conveniently, the grounding means electrically grounds the holder by connecting the holder to ground via the location means.

When the centrifugal device according to the present invention is used in conjunction with a liquid handling robot, it is often required to detect the level of liquid within the holder. Detection of the liquid level in the holder is typically carried out using a capacitance measurement system, the measuring electrode comprising a pipette used to dispense liquid into the holder. In such a situation, it is important that there is a good quality reference plane close to the measuring electrode in order that a correct measurement can be obtained thus allowing accurate detection of the liquid level in the holder.

A good quality reference plane should be positioned close to the measuring electrode (pipette) and should be connected to the capacitance measurement system by a low ohmic connection.

By means of the grounding means, therefore, it is possible to electrically ground the holder.

Preferably, when the device comprises two holding pins, the holding pins are positioned substantially diametrically opposite one another.

Advantageously, the holder has a rest position in which the holder axis is substantially parallel with, but slightly off-set from the rotor axis, and a swing position in which the holder axis forms a non-zero angle with the rotor axis, the device further comprising a first swing stop pin for limiting the non-zero angle of the swing position.

By means of the present invention, a single swing out type sample holder is suspended towards the centre of the centrifugal device by holding pins positioned on either side of the holder. This allows the holder to swing about the axis of the pin or pins, which axis is substantially perpendicular to and intersects with the rotor axis. After rotation, the sample holder swings back to its original position. The fact that the position of the sample holder, and therefore the position of the sample container is fixed before and after centrifugation allows the standard overhead robot pipette to perform sample loading and extraction. The vertical resting position of the sample holder also allows the pipette full, unhindered access to the sample container.

The first swing stop pin ensures that the swing movement of the sample holder is limited. This prevents the sample holder from swinging out to a horizontal position relative to the rotor axis which may be undesirable in certain cases.

Conveniently, the device further comprises a second swing stop pin for similarly limiting the extent of the swing of the sample holder in the opposite sense.

Alternatively, the device comprises a rest stop for preventing swing movement of the holder in one sense.

The relative centrifugal force exerted on a sample is determined by the product of the spin radius (the distance between the sample and the centre of the rotor) and the speed of rotation squared.

In the embodiment of the invention described hereinabove, the centrifugal force will be restricted by the relatively small spin radius of the sample holder. This will however be sufficient for many applications such as cell sedimentation.

Advantageously, the centrifugal device further comprises guide means for guiding the holding pin from a first, rest position, to a second, swing position, the position of the holding pin in the second position being spaced apart from and substantially parallel to the location of the pin when in the first position.

Advantageously the guide means comprises a guide channel in which the or each holding pin is located.

Once rotation begins, the centrifugal force causes the sample holder to slide from the first position to the second position before, or substantially at the same time as, the sample swings out. A slight angling of the guide channel from the horizontal, or the use of a light spring, ensures that when the centrifuge stops, the sample holder returns to its rest position and can be accessed by a robot pipette. This embodiment of the invention provides a greater centrifugal force.

In centrifugation it is important to ensure that the rotor is balanced to allow smooth running and to prevent damage to the rotor. In many applications, where the sample mass and centrifugation speed is low, the rotor is effectively balanced. However, if the sample mass or rotation speed are high it may be necessary to actively balance the device.

Under such circumstances, the device advantageously further comprises a balance in the form of a balance tube. The balance tube is free to pivot about the same holding pin as the sample holder, and is arranged to swing out in the opposite direction to the sample holder.

Advantageously, the device further comprises a first balance stop pin for restricting the swing out movement of the balance. The balance stop pin is located in a corresponding position to that of the swing stop pin. The balance tube has substantially the same mass as the sample holder and should be capable of being filled with a fluid such as water in order that it may have the same mass as the overall mass of the sample, container, holder and sample tube.

Preferably, the device further comprises a second balance stop pin which restricts the movement of the balance tube towards to the centre of the centrifuge. This ensures that the sample tube can occupy a central, pipette accessible position when in the rest position.

Although the individual holders have been described as separate entities to the containers, it is to be understood that the locating means could be adapted to directly receive a container, obviating the need for holders.

According to a second aspect of the present invention, there is provided a robot platform comprising a centrifugal device comprising:
    a rotor having a rotor shaft having a longitudinal rotor axis;
    a holder having an access end, and a holder axis;
    location means for locating the holder within the centrifugal device, such that the holder is rotatable about the rotor axis, with the holder axis forming a non-zero angle with the rotor shaft axis, the location means accurately locating the access end of the holder within the centrifugal device, wherein: the location means comprises a holding pin having an axis that is substantially perpendicular to the rotor axis, the holding pin being rotatable about the rotor axis; and the holder having a holder radius, the axis of the holding pin being spaced apart from the rotor axis by a distance that is less than the holder radius.

According to a third aspect of the present invention, there is provided an apparatus for filling a container with a material, the apparatus comprising:
    a robotic pipette;
    a robotic platform comprising a centrifugal device comprising:
    a rotor having a rotor shaft having a longitudinal rotor axis;
    a holder having an access end, and a holder axis;
    location means for locating the holder within the centrifugal device, such that the holder is rotatable about the rotor axis, with the holder axis forming a non-zero angle with the rotor shaft axis, the location means accurately locating the access end of the holder within the centrifugal device, wherein: the location means comprises a holding pin having an axis that is substantially perpendicular to the rotor axis, the holding pin being rotatable about the rotor axis; and the holder having a holder radius, the axis of the holding pin being spaced apart from the rotor axis by a distance that is less than the holder radius.

Advantageously, the apparatus for filling a container further comprises grounding means for electrically grounding the holder.

Preferably, the grounding means electrically grounds the holder by connecting the holder to ground via the location means.

Preferably, the ground means electrically grounds the holder by connecting the holder to the robotic platform via the location means.

In such an apparatus, the robotic pipette forms a measuring electrode.

According to a fourth aspect of the present invention, there is provided a method of transferring a sample of material into a container located within a holder using an apparatus for filling a container with a material, the apparatus comprising:
    a robotic pipette;
    a robotic platform comprising a centrifugal device comprising:
    a rotor having a rotor shaft having a longitudinal rotor axis;
    a holder having an access end and a holder axis;
    location means for locating the holder within the centrifugal device, such that the holder is rotatable about the rotor axis, with the holder axis forming a non-zero angle with the rotor shaft axis, the location means accurately locating the access end of the holder within the centrifugal device, wherein the location means comprises a holding pin having an axis that is substantially perpendicular to the rotor axis, the holding pin being rotatable about the rotor axis; and the holder having a holder radius, the axis of the holding pin being spaced apart from the rotor axis by a distance that is less than the holder radius;

the method comprising the steps of:

loading a pipette with the material;

moving the pipette to the container;

dispensing the material into the container.

BRIEF DESCRIPTION OF THE DRAWINGS

The invention will now be further described by way of example only with reference to the accompanying drawings in which.

DESCRIPTION OF THE PREFERRED EMBODIMENT

Figure 1:
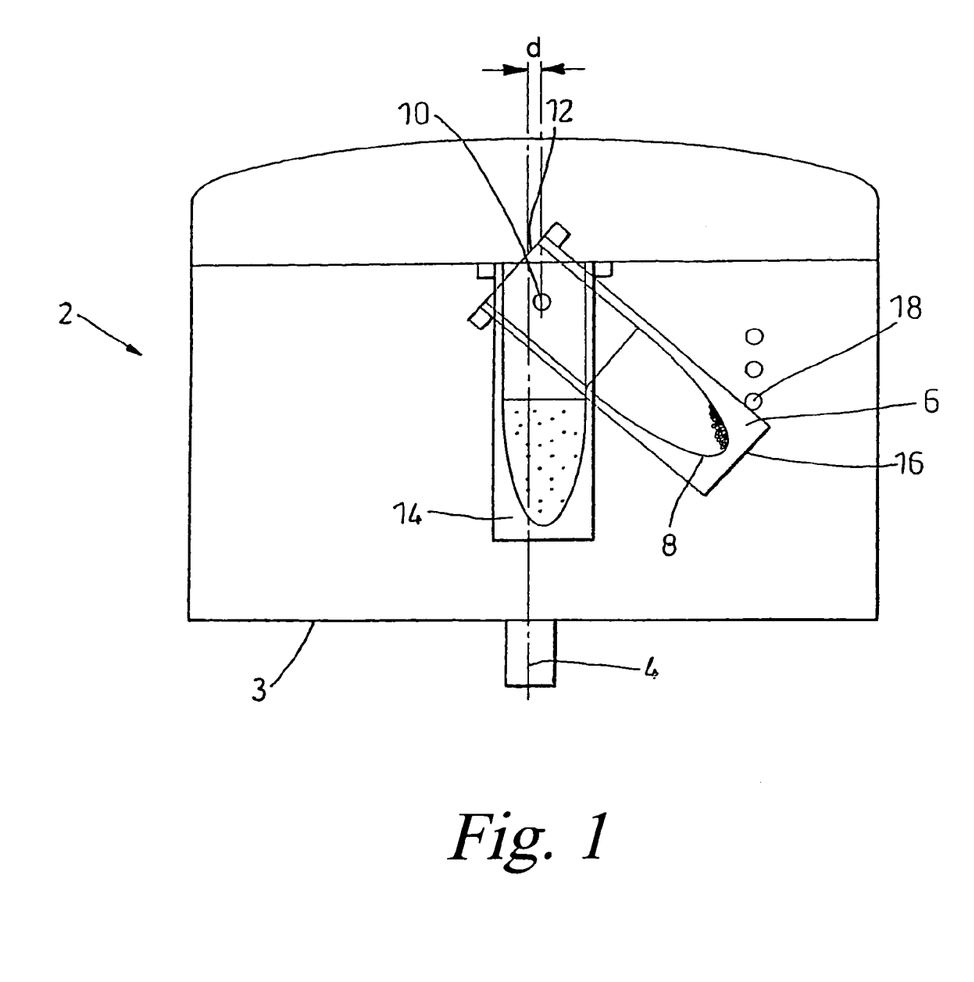
FIG. 1 is a schematic representation of a centrifugal device according to the present invention which is compatible with a pipetting robot.

Turning now to FIG. 1, a centrifugal device according to a first embodiment of the present invention is designated generally by the reference numeral 2. The centrifugal device comprises a rotor shaft 4 positioned at the centre of the centrifuge device and about which the centrifugal device 2 is rotatable, and a rotor body 3. The device 2 further comprises a sample holder 6 adapted to hold a sample container 8. The sample holder is attached to the centrifugal device by means of one or more holding pins 10 having an axis which is perpendicular to the axis of the rotor shaft 4. The holding pin is rotatable about the rotor shaft 4. The sample holder 6 comprises an access end 12 allowing access to the interior of the sample holder 6 by, for example, a pipette.

In use, a motor (not shown) rotates the centrifugal device 2 about the rotor shaft 4. Centrifugal forces cause the sample holder 6 to swing out from the position depicted by the reference numeral 14 to the position depicted by the reference numeral 16.

As can be seen, in the rest position 14 the sample holder is aligned with the rotor shaft, whereas in the swing out position 16, the sample holder is angled to the rotor shaft 4.

The extent of swing of the sample holder 6 is limited by a swing stop pin 18. The position of the swing stop pin may be varied depending on the properties of the sample.

The holder axis is slightly offset from the longitudinal rotor axis by a distance "d" which is less than the holder radius as shown in FIG. 1, or weighted on the outside so that when rotation starts, the centrifugal force developed will cause the holder to swing out at an angle in a well defined direction. This allows for an appropriate counter-weight balance to be calculated and accounted for in the rotor, such that correct balancing of the rotor during centrifugation is obtained when handling a small liquid volume.

As can be seen, the access end 12 of the sample holder 6 is accurately located by the holding pin 10. Both before and after rotation, the sample holder assumes a rest position depicted by position 14, in which the access end 12 has the same position. This allows easy access to the sample holder by a pipetting robot, since the location of the access end 12 is constant both before and after rotation.

In addition, because the longitudinal axis of the sample holder 6 is substantially parallel with the rotor axis in the rest position, a pipetting robot will have unhindered access to the access end 12 of the sample holder 6.

Figure 2:
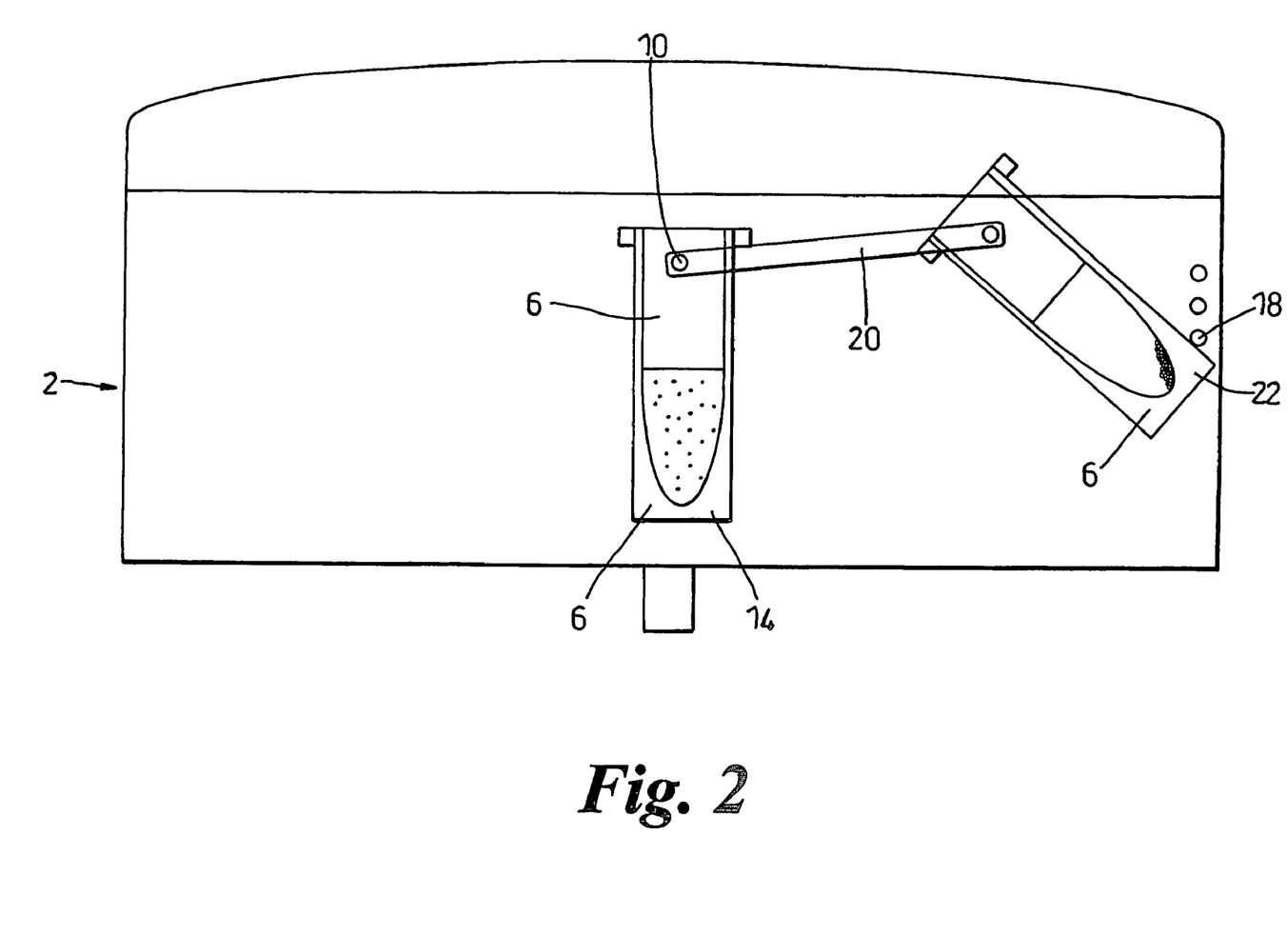
FIG. 2 is a schematic representation of a second embodiment of the invention also compatible with a pipetting robot.

Turning now to FIG. 2, a second embodiment of the invention is shown. Similar parts to those described with reference to FIG. 1 have been given corresponding reference numerals for the sake of clarity.

The centrifugal device 2 further comprises a guide channel 20 within which the holding pin 10 is moveable. During use, once rotation of the device 2 has commenced, the sample holder 6 will move from the rest position 14 to a position not shown in FIG. 2, which is substantially parallel to and spaced apart from position 14. This movement is possible, through movement of the holding pin 10 along the channel guide 20. As the sample holder 6 moves, it also swings out due to the effect of the centrifugal force to take up position 22. This arrangement may be preferred when a greater centrifugal force is required. Movement of the holder 6 is restricted by a swing stop pin 18.

Figure 3:
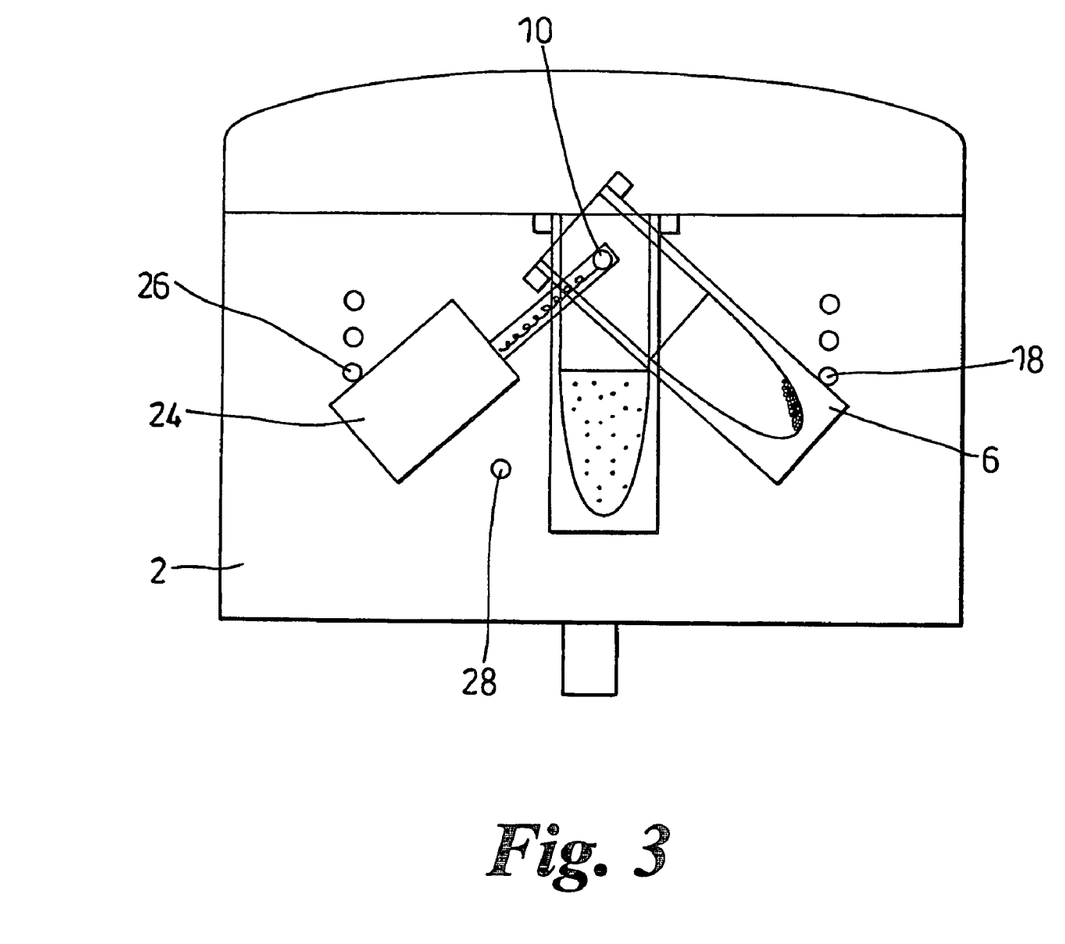
FIG. 3 is a schematic representation of a third embodiment of the present invention also compatible with a pipetting robot.

Turning now to FIG. 3, a third embodiment of the invention is shown. Again, for the sake of clarity, those parts which are common to the embodiments shown in FIGS. 1 and 2 have been given corresponding reference numerals. The centrifugal device 2 further comprises a balancing tube 24 which may be advantageous to allow smooth running, and to prevent damage of the rotor in cases where the sample mass is high relative to the rotor mass, and the centrifugation speed is high. The balance tube is free to pivot about the holding pin 10 and is arranged to swing out in the opposite direction to the sample holder 6. Movement of the balance tube 24 is restricted by a balance stop pin 26 which is positioned at a corresponding angle to the swing stop pin 18. The balance tube has substantially the same mass as the sample holder 6, and is capable of being filled with water in order that it has the same mass as the sample holder, sample tube and sample combined.

In order to ensure that the sample holder 6 can occupy a central pipette accessible position when in the rest position, the balance tube 24 is restricted in its movement towards the centre of the centrifuge by a balance rest stop pin 28.

Although balancing of the sample holder has been shown in terms of the embodiment shown in FIG. 1, balancing of the embodiment shown in FIG. 2 can be achieved in a similar manner.

The centrifugal device according to the present invention may be used in connection with a liquid handling robot. In such situation, a liquid detection mechanism may also be used to detect the level of a liquid held in the sample container 8. Liquid level detection is usually carried out using a capacitance measurement. When using a liquid handling robot, liquid is dispensed into the sample container 8 by means of a pipette controlled by the robot. When liquid level detection is carried out using capacitance measurement, the pipette comprises a measuring electrode. In order to obtain accurate measurements of the level of liquid in the sample container 8, it is necessary to ensure that there is a good quality reference plane close to the measuring electrode.

Figure 4:
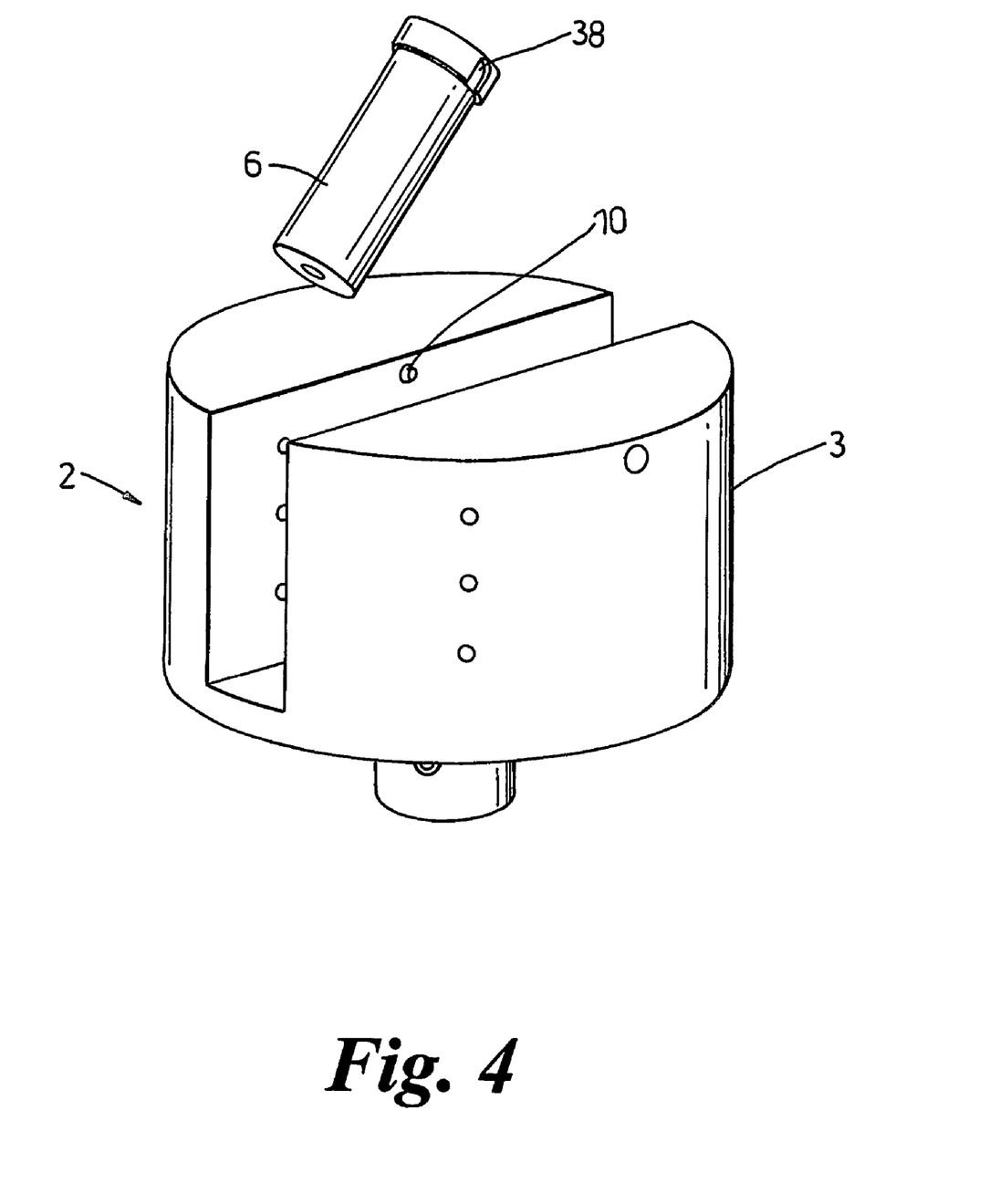
FIG. 4 is a schematic representation of a fourth embodiment of the invention in which the holding pin extends from the rotor body.

Turning to FIG. 4, a further embodiment of the invention is shown. Parts that correspond to those shown in FIGS. 1 to 3 have been given corresponding reference numerals for each of reference.

In the embodiment shown in FIG. 4, two holding pins 10, only one of which is shown, extend from the rotor body 3. The sample holder 6 comprises two recesses 38 (only one of which is shown). The holding pins 10 are engageable with the recesses 38 to support the sample holder 6.

In order to achieve accurate measurement of the liquid level, it is advantageous to connect the sample holder 6 to a ground signal which may comprise a robot platform, for example, via the one or more holding pins 10.

Two further embodiments of the invention comprising a grounding means for connecting the sample holder 6 to a ground signal in the form of, for example, a robot platform, via a holder pin 10 are described further hereinbelow with reference to FIGS. 5 and 6. Those parts of the device 2 which correspond to parts shown in the embodiments of the invention shown in FIGS. 1 to 3 have been given corresponding reference numerals for ease of understanding.

Figure 5:
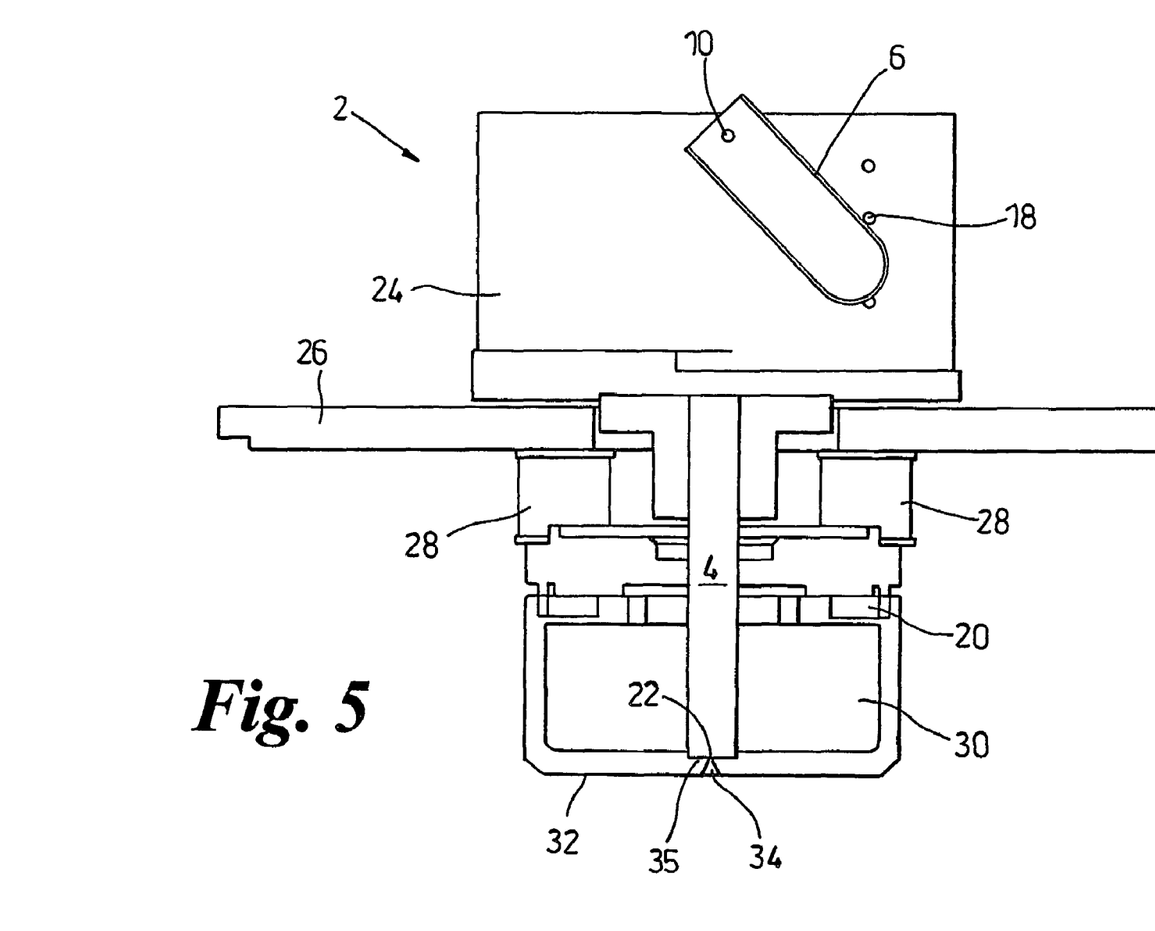
FIG. 5 is a schematic representation of the fourth embodiment of the present invention including grounding means.

Referring first to FIG. 5, a centrifuge device according to the present invention is designated generally by the reference numeral 2. The device comprises a spring loaded pole 32 which is mounted in the static site 20 of a motor used to power the device 2. The pole 32 extends under the device 2 towards the centre of the rotor shaft 4 such that it comes into contact with an end 22 of the shaft. The end 22 comprises the moving site of the motor, and the pole 32 makes contact with the end 22 via a coal collector shoe 34. The rotor shaft 4 is typically made of iron. However, in order to obtain a good contact between the rotor shaft 4 and coal collector shoe 34, the shaft is preferably formed from a brass material. For example, the shaft 4 could be formed from a thin brass plate mounted at the end of the shaft 4 by means of one or more screws.

Figure 6:
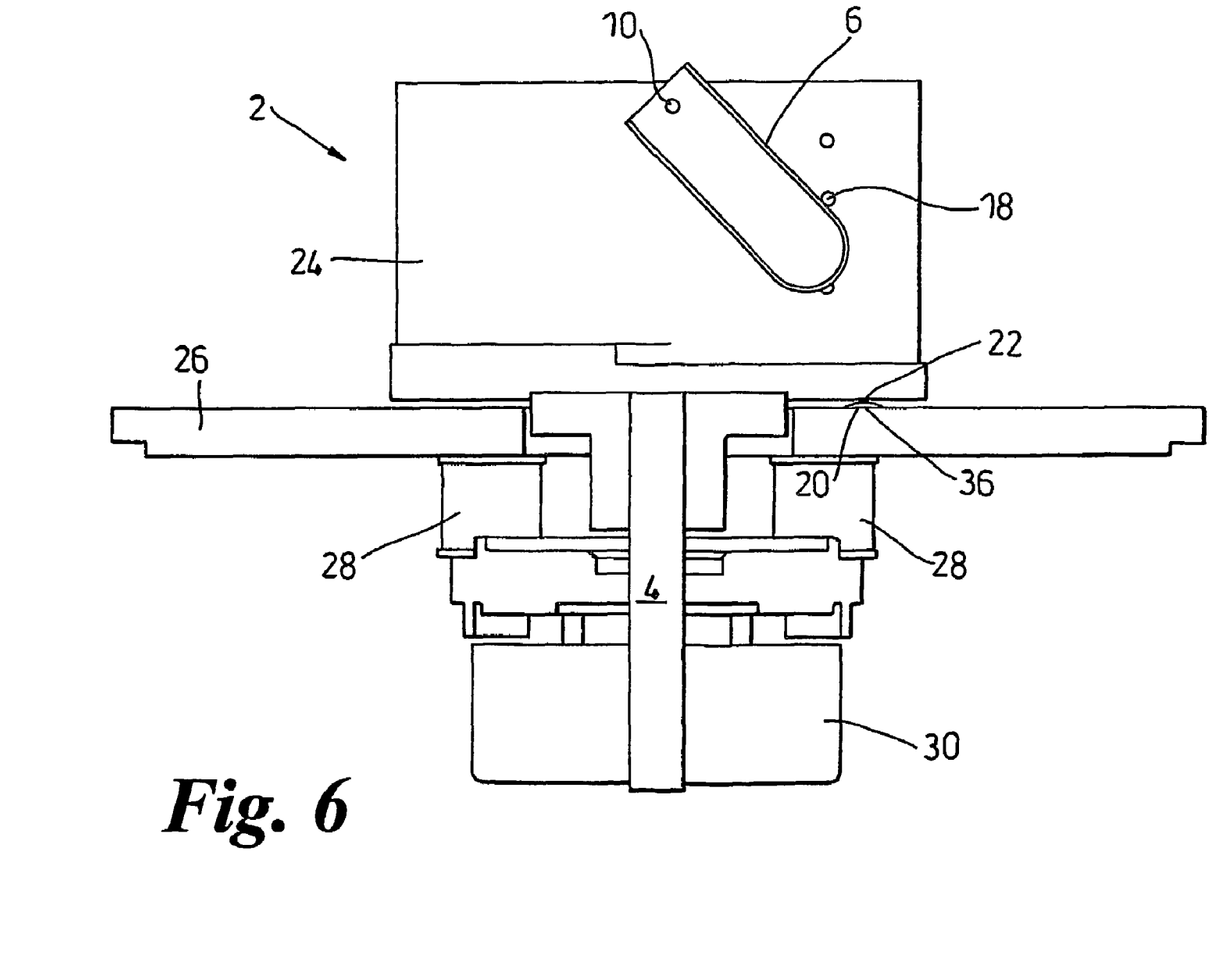
FIG. 6 is a schematic representation of a fifth embodiment of the present invention also containing grounding means.

Turning now to FIG. 6, a further embodiment of the invention is shown. In this embodiment, the spring loaded pole 36 is mounted directly onto a robot platform 26 such that it is positioned under the rotor body 3. The spring loaded pole 36 is therefore, connected to the static site of the motor. The pole 36 then extends along an underneath side of the rotor body 3 and takes the form of a trolley pole. A coal collector shoe 34 is mounted at the end of the trolley pole. In order to obtain a good contact between the spring loaded pole and the rotor body 3, the coal collector shoe is preferably formed, at least partially, from brass.

In both of the embodiments illustrated in each of FIGS. 5 and 6, the sample holder 6, the holding pins 10, the robot platform 26 and the rotor body 24 are each made of conducting material, or at least incorporate paths of conducting materials such as wires, within them, in order to establish an electrical connection between the components.

The two illustrated embodiments of the invention allow a good electrical connection to be formed between a static robot platform 26 which represents a good reference plane, and the rotor body 3, which is the moving part of the centrifuge.

The main difference between the two embodiments shown in FIGS. 5 and 6 is that, in the embodiment shown in FIG. 5, the speed applied to the coal collector shoe 34 by the shaft 4 is much smaller than the speed applied to coal collector shoe 34 in the embodiment illustrated in FIG. 6. This is because in the embodiment shown in FIG. 5, the coal collector shoe 34 touches the centre of the shaft 4 only, whereas in the embodiment shown in FIG. 6, the coal collector shoe 34 is in contact with the rotor body 3. The lifetime of the coal collector shoe 34 in the embodiment shown in FIG. 6 will therefore, be shorter than the lifetime of the coal collector shoe 34 as used in the embodiment illustrated in FIG. 5.

Figure 7:
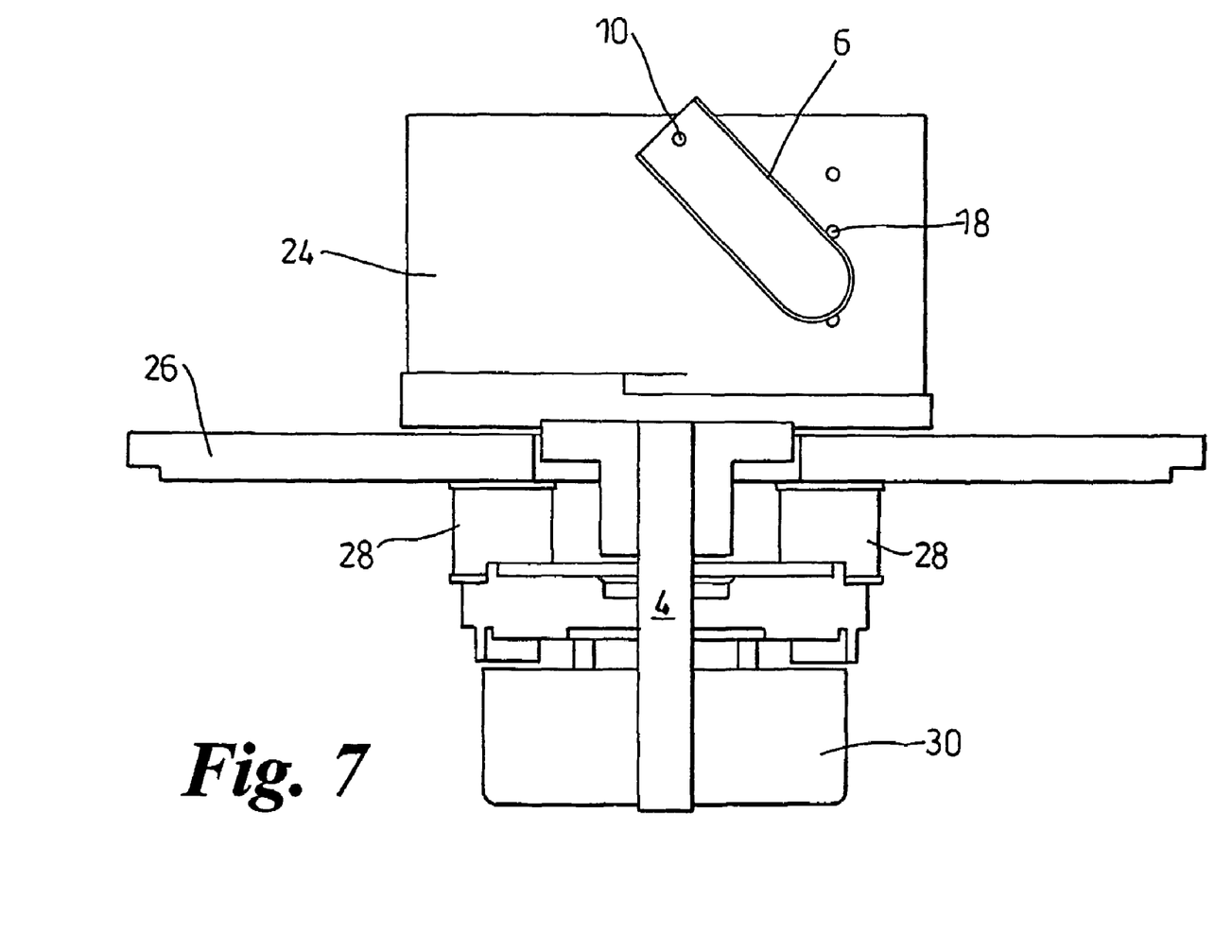
FIG. 7 is a schematic representation of a sixth embodiment of the present invention incorporating a vibration absorber.
Figure 8:
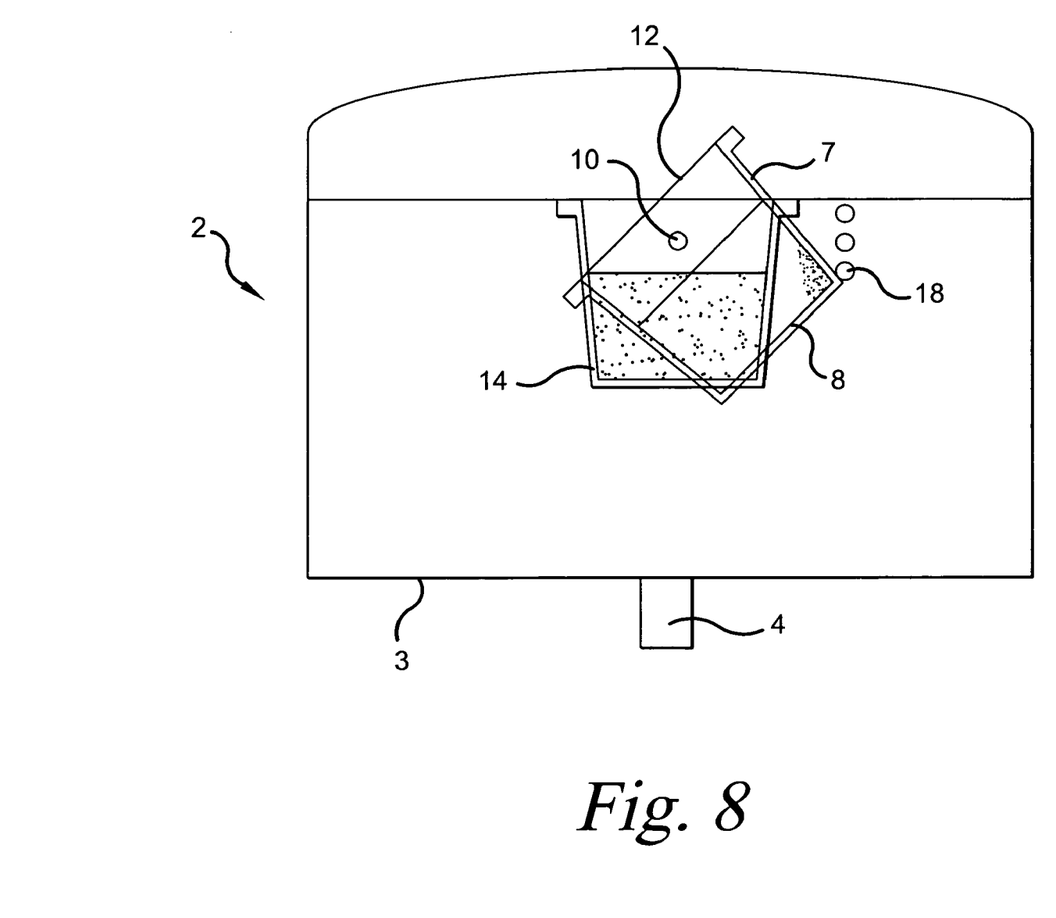
FIG. 8 is a schematic representation of a centrifugal device according to the present invention where the holder 6 is replaced with a bucket 7.

Turning now to FIG. 7, a further embodiment of a centrifuge device according to the present invention is shown.

In certain circumstances, operation of the device 2 may result in vibration. If sensitive components are positioned on the robot platform 4, it is important to minimise the vibrations. The shape of the rotor body 3 can influence the level of vibration experienced during operation of the device 2.

In order to further minimise vibrations, it is necessary to calculate the balance, or counterweight of the rotor body 3 with a nominal load i.e., with a nominal fluid in a sample container 8 positioned in holder 6, and a nominal angle of swing of the sample holder 6. Vibrations will be minimised if the device as a whole is balanced.

In addition, rubber suspensions 28 may be included in the centrifuge device 2. In the embodiment illustrated in FIG. 7, four rubber suspensions 28 are present, with one rubber suspension being positioned in each corner of the motor, such that the centrifuge has no direct and/or hard connections with the robot platform. The rubber suspensions dampen most, or all remaining vibrations transmitted to the robot platform 26.

The invention claimed is:

1. A centrifugal device comprising:
    a rotor having a rotor shaft having a longitudinal rotor axis;
    a holder having an access end, and a holder axis;
    location means for locating the holder within the centrifugal device, such that the holder is rotatable about the rotor axis, with the holder axis forming a non-zero angle with the rotor shaft axis, the location means accurately locating the access end of the holder within the centrifugal device, wherein: the location means comprises a holding pin having an axis that is substantially perpendicular to the rotor axis, the holding pin being rotatable about the rotor axis; and the holder having a holder radius, the axis of the holding pin being spaced apart from the rotor axis by a distance that is less than the holder radius.

2. A centrifugal device according to claim 1 comprising two holding pins, which holding pins are coaxial with one another.

3. A centrifugal device according to claim 2 wherein the holder comprises one or more recesses engageable with the or each holding pin.

4. A centrifugal device according to claim 2, or any claim dependent thereon wherein the two holding pins are positioned diametrically opposite each other.

5. A centrifugal device according to claim 1 wherein the or each holding pin extends from the holder, and is positioned towards the access end of the holder.

6. A centrifugal device according to claim 1 wherein the or each holding pin extends from the rotor.

7. A centrifugal device according to claim 1 further comprising grounding means for electrically grounding the holder.

8. A centrifugal device according to claim 7 wherein the grounding means electrically grounds the holder by connecting the holder to ground via the location means.

9. A centrifugal device according to claim 1, further comprising absorption means for absorbing vibration created during use of the device.

10. A centrifugal device according to claim 9 wherein the absorption means comprises one or more rubber components.

11. A centrifugal device according to claim 1 wherein the holder has a rest position in which the holder axis is substantially parallel with the rotor axis, and a swing position in which the holder axis forms a non-zero angle with the rotor axis, the device further comprising a first swing stop pin for limiting the non-zero angle of the swing position.

12. A centrifugal device as claimed in claim 11 further comprising a second swing stop pin.

13. A centrifugal device as claimed in claim 1 further comprising a rest stop for preventing rotation of the holder about the holding pin in one direction.

14. A centrifugal device as claimed in claim 1 further comprising guide means for guiding the holding pin from a first, rest position, to a second, swing position, such that when the holding pin is in the second position it is spaced apart from and substantially parallel to the location of the holding pin when in the first position.

15. A centrifugal device as claimed in claim 1 further comprising a balance.

16. A centrifugal device as claimed in claim 15 further comprising a balance stop pin.

17. A centrifugal device as claimed in claim 16 further comprising a balance rest stop pin.

18. A centrifugal device as claimed in claim 1 wherein the holder comprises a tube.

19. A centrifugal device as claimed in claim 1 wherein the holder comprises a bucket.

20. A robot platform comprising a centrifugal device according to claim 1.

21. Apparatus for filling a container with a material, the apparatus comprising:
   a robotic pipette;
   a robot platform according to claim 20.

22. A method of transferring a sample of material into a container using the apparatus of claim 21, wherein the container is located within the holder, comprising the steps of:
   loading a pipette with the material;
   moving the pipette to the container; and
   dispensing the material into the container.

* * * * *